(12) United States Patent
Thomas et al.

(10) Patent No.: US 11,298,047 B1
(45) Date of Patent: Apr. 12, 2022

(54) METHOD FOR DISPLAYING RELATIVE POSITION INFORMATION OF AN ENDOSCOPE IMAGE

(71) Applicant: Asensus Surgical US, Inc., Durham, NC (US)

(72) Inventors: Bradley Scott Thomas, Cary, NC (US); Brian P Cash, Cary, NC (US)

(73) Assignee: Asensus Surgical US, Inc., Durham, NC (US)

( * ) Notice: Subject to any disclaimer, the term of this patent is extended or adjusted under 35 U.S.C. 154(b) by 0 days.

(21) Appl. No.: 17/064,196

(22) Filed: Oct. 6, 2020

(51) Int. Cl.
| | |
|---|---|
| *A61B 34/20* | (2016.01) |
| *A61B 5/107* | (2006.01) |
| *H04N 13/254* | (2018.01) |
| *H04N 13/324* | (2018.01) |
| *G06T 7/521* | (2017.01) |
| *G06T 7/593* | (2017.01) |
| *A61B 1/05* | (2006.01) |
| *A61B 1/00* | (2006.01) |

(Continued)

(52) U.S. Cl.
CPC ........ *A61B 5/1076* (2013.01); *A61B 1/00045* (2013.01); *A61B 1/05* (2013.01); *A61B 1/0676* (2013.01); *A61B 5/1077* (2013.01); *A61B 5/1079* (2013.01); *G06T 7/521* (2017.01); *G06T 7/593* (2017.01); *H04N 13/239* (2018.05); *H04N 13/254* (2018.05); *H04N 13/324* (2018.05); *A61B 1/00193* (2013.01); *A61B 2090/366* (2016.02); *G06T 2207/10012* (2013.01); *G06T 2207/10068* (2013.01); *H04N 2013/0081* (2013.01)

(58) Field of Classification Search
CPC . A61B 5/1076; A61B 1/0676; A61B 1/00045; A61B 5/1077; A61B 1/05; A61B 5/1079; A61B 2090/366; A61B 1/00193; H04N 13/254; H04N 13/324; H04N 13/239; H04N 2013/0081; G06T 7/521; G06T 7/593; G06T 2207/10068; G06T 2207/10012
See application file for complete search history.

(56) References Cited

U.S. PATENT DOCUMENTS

| | | | |
|---|---|---|---|
| 6,503,195 B1 * | 1/2003 | Keller ................ | A61B 1/00193 348/45 |
| 2005/0219552 A1 * | 10/2005 | Ackerman ........... | H04N 13/254 356/603 |

(Continued)

*Primary Examiner* — Howard D Brown, Jr.

(57) ABSTRACT

Imaging methods aid a user in understanding relative depths of objects or topography within a field of view. In one method, image data is gathered using 3D image sensors, while illumination of an area of interest is alternated with projection of a pattern onto the area of interest. The captured image data is used to display a 3D true color image; a monochrome grid on surfaces of the area of interest; a 3D true color image with a monochrome grid on surfaces of the area of interest; a 2D or 3D false color image where different colors identify different depths of regions of the area of interest; and/or a 2D or 3D true color image of an area of interest with features in the area of interest located a first depth relative to the image sensors highlighted with a common color. In another method, 3D image data is used to generate a 2D image that highlights features at a common depth using the same color.

8 Claims, 3 Drawing Sheets

(51) Int. Cl.
*A61B 1/06* (2006.01)
*H04N 13/239* (2018.01)
*A61B 90/00* (2016.01)
*H04N 13/00* (2018.01)

(56) References Cited

U.S. PATENT DOCUMENTS

2020/0195903 A1* 6/2020 Komp .................. H04N 13/156
2021/0145523 A1* 5/2021 Xing ........................ G06T 7/73

* cited by examiner

METHOD FOR DISPLAYING RELATIVE POSITION INFORMATION OF AN ENDOSCOPE IMAGE

BACKGROUND

Three dimensional imaging systems are commonly used in laparoscopic and endoscopic surgery to produce a 3D image of the operative site. Although it is useful for allowing a user to simulate depth perception during surgery for difficult tasks such as suturing or tissue approximation, its output is typically qualitative in nature. Furthermore, the 3D effect is distracting and uncomfortable for some users, and can add to fatigue and eyestrain. The present application describes alternatives to traditional 3D imaging that allow visualization of tissue topography or the relative positions of objects etc within the body cavity.

Note that the term "endoscope" is used in this application in a generic sense and is not intended to exclude scopes used outside of endoscopic procedures, such as laparoscopes. Moreover, while described in the context of surgery, the embodiments described herein may be used for a variety of applications outside of surgery.

DETAILED DESCRIPTION

Imaging System with 3D Scanner Overlay

Disclosed herein is a system that combines 3D scanner technology with the 3D stereo imaging. There are multiple technologies used for 3D scanner digitizing of objects. For example, U.S. Pat. No. 4,645,917 (incorporated herein by reference) describes a swept aperture flying spot profiler. It uses a rapidly scanned laser spot with a combination of de-scanning and triangulation angle to measure the distance to an object at thousands of points in the field of view. The single point reading and wide dynamic range photo detector of that system made it immune to surface reflectivity changes and external interference. Scanned laser digitizers are known in art, but more common are structured light scanners used for 3D scanning and 3D topography. These project either a moving stripe of light or a grid of light onto the object. The source is usually a laser with a holographic diffuser image generator which can project a grid, stripes, or dots at a diverging angle. The further away the object on which the pattern is illuminated, the larger the projected pattern becomes. The pattern density and divergence angle is controlled by the holographic element design. Imaging this projected grid with two cameras provides a stereo image where the grid spacing on the surface can be directly translated to distance to that surface.

Figure 1A:
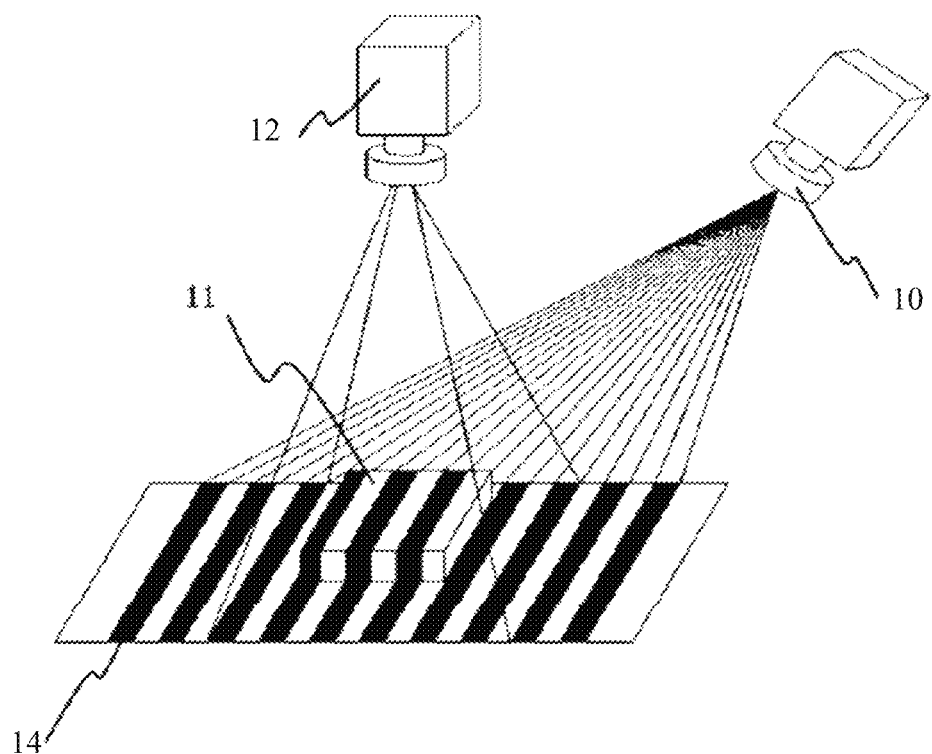
FIGS. 1A and 1B are diagram schematically illustrating use of a stripe projector.
Figure 1B:
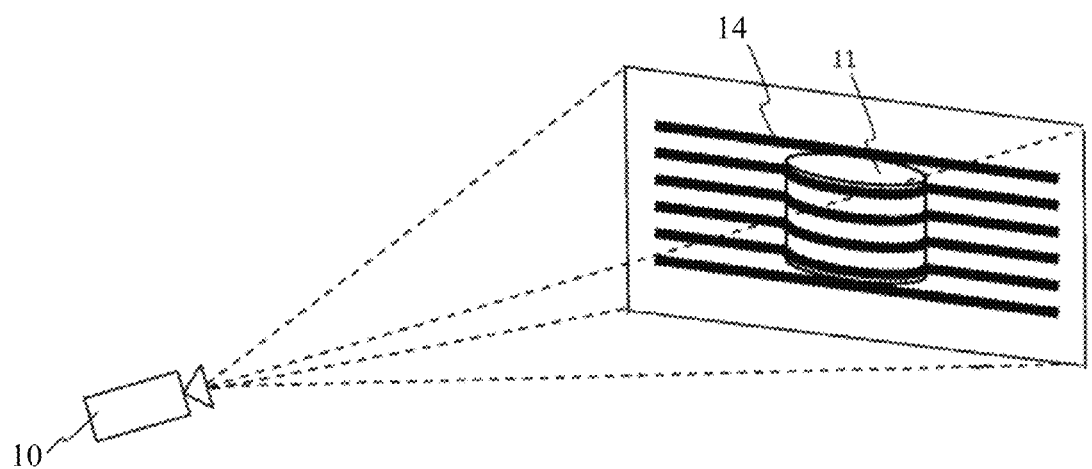

FIGS. 1A and 1B are diagrams schematically illustrating use of one example of a stripe projector 10 projecting a stripe pattern 14 onto an object 11, and a camera 12 capturing images of the object 11. As shown, the spacing between the stripes changes with the distance from the projector, and the stripes can be seen to curve as they wrap around objects 11. Examples of a small, portable, scanners that might be used for the present system are the LaserDesign Rexcan DS2 and the Creaform HandyScan 3D handheld scanner.

Figure 2:
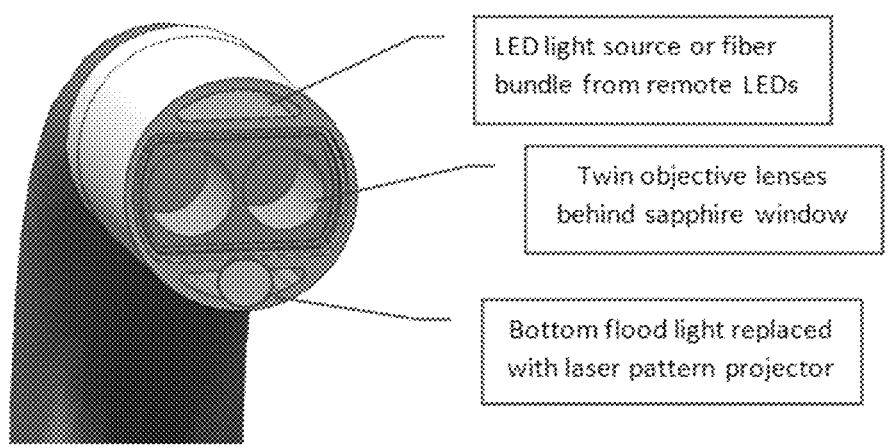
FIG. 2 shows an endoscopic or laparoscopic imaging head of the first embodiment.

An embodiment of system according to the present invention is a surgical endoscope, laparoscope, or the like that combines a laser grid projector with the existing stereo vision camera. FIG. 2 shows one embodiment of the 3D imaging head of a surgical scope incorporating the features described herein. The imaging head of the scope may be one that is actively steerable or articulatable using actuation mechanisms of a type known to those skilled in the art.

The imaging head includes twin parallel objective lenses behind a sapphire window, and a pair of imagers (e.g. CMOS image sensors). A light source, which may be an LED light source or a fiber bundle carrying light from remote LEDs, is positioned to illuminate the imaging field. A laser pattern projector (e.g. a laser diode with a holographic grid projection element adjacent to it) is positioned to project a grid pattern or some other pattern onto the objects/tissues within the imaging field. The FIG. 2 embodiment is but one example of an arrangement of these elements on an imaging head, and it should be understood that alternate arrangements may instead be used without departing from the scope of the present invention. In use of the system, the imagers of the 3D system are operated at 60 Hz or another suitable frequency. The imaging system's white illumination LEDs and the laser of the pattern projector are turned on only during alternating frames, allowing capture of both real color images (during white illumination) and the depth triangulation grid (when the laser is activated) for independent usage.

The captured image data is captured by the imagers and processed by the associated image processing system. The processed image displayed to the user could be any of the following:

1. 3D true color image (even frames)
2. Monochrome grid on surfaces (odd frames)
3. 3D true color image with monochrome grid on surfaces (add frames)
4. 2D or 3D false color image where colors map to depth
5. 2D or 3D true color image with objects at the instrument tip depth are highlighted with the same color as the tip (i.e. A blue highlighted duct and a blue clip applier tip indicates that they are at the same depth)

An advantage of the system of the first embodiment is that it presents 3D data while not requiring the user to view the image in 3D. This is beneficial because the 3D monitor with polarized glasses is not suitable for all people. Those with limited or no vision in one eye cannot see the 3D image, and others struggle to get the parallax angle to work and have trouble making the 3D appear to pop out. Still others experience nausea when viewing 3D displays. This concept can add 3D looking grids and/or false color enhancements to either the 2D or 3D display to convey the depth information.

Displaying Relative Position Information on an Endoscopic Image

The second embodiment comprises a method whereby data obtained from a 3D imaging system is used to generate a 2D video image that offers a useful means of determining relative depth of instruments or other medical devices with respect to tissue or other objects.

It is possible to create a 3D model of a scene, such as a surgical field, using trigonometric data calculated from a 3D image obtained using an endoscope. Methods and systems for generating such a model are described in literature. For example, the stereoscopic 3D imaging system may use two imagers with parallel objective lenses. These may be separated by 5 mm to create parallax similar to our eye separation. When the left and right images are overlaid, any vertical edges at infinity will be coincident and at zero distance from the objective will be seen as double edges 5 mm apart. Closer objects have more separation in the left and right images than further objects. Thus an algorithm may be used to find the same edge of an object, get the offset in pixels, and calculate the approximate distance in mm. Additional input is obtained from another form of remote sensing technology, such as LIDAR or SONAR to construct a mathematical representation of the 3D intra-operative space.

Figure 3:
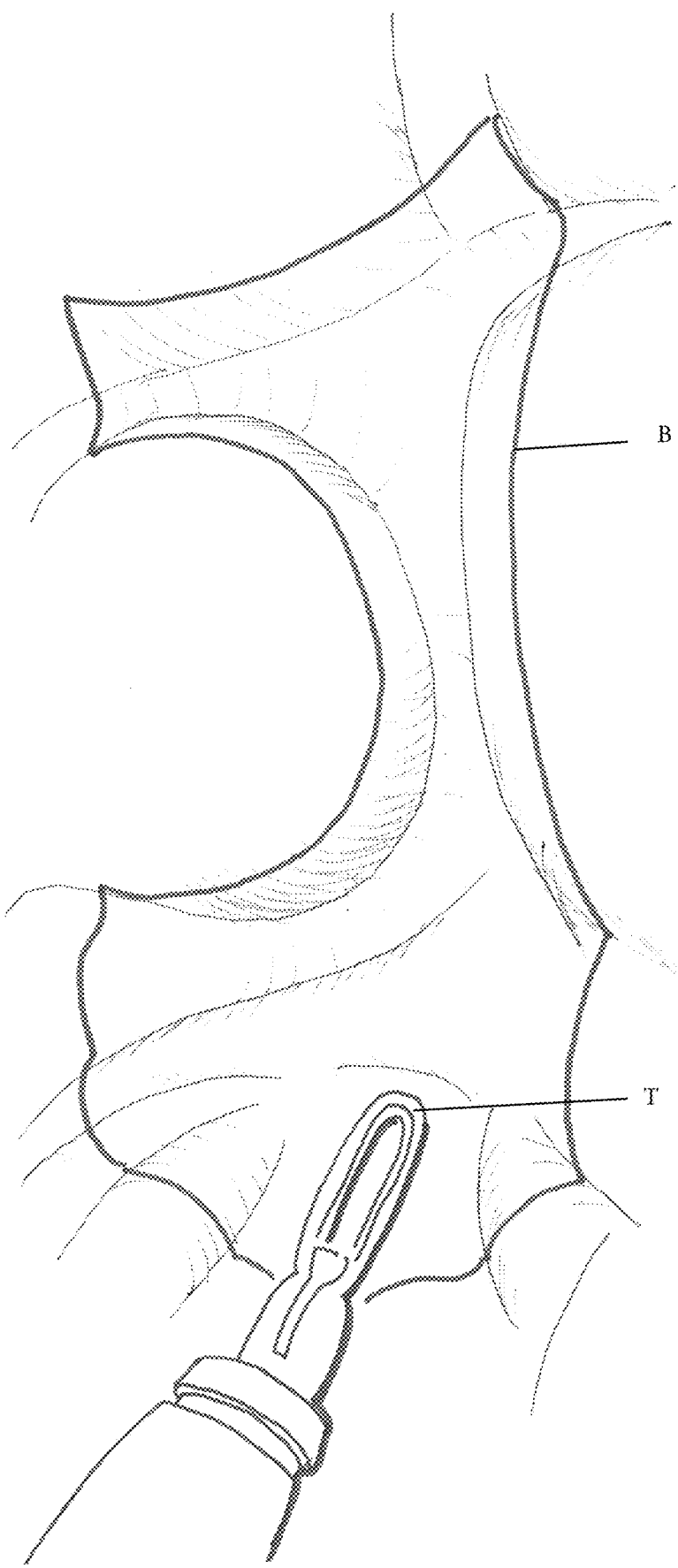
FIG. 3 shows a type of color map that can be generated using methods of the second embodiment.

These data are then used by the system to derive the plane, parallel to some user reference frame (e.g. the image plane of the imaging system) which contains a point corresponding to the instrument tip. Thus, the position of the instrument tip relative to the tissue is known. Through graphics processing software, a two dimensional image is produced on which any tissue that are within the plane of the instrument tip are selectively colored with an artificial and obvious color that is different from surrounding tissue (bright blue or green, for example). An example of such an image is shown in FIG. 3, in which the colored border B marks tissue at the same depth as the tip T of the surgical instrument. As the tip T is moved within the body cavity, the image continually updates to visually indicate to the user what tissues lay in the plane of the instrument tip. This gives the user an obvious indication of what tissue is able to be manipulated at any point in the depth of the working space. In one embodiment, a gradient of hues or colors that correspond to known distances from the "working-depth plane" described above may be used in lieu of a single colored plane. As another example, if a surgical clip applier in use for surgery is positioned at the same depth as the patient's bile duct, the image display might show both the duct and the clip applier shaded with the same color.

We claim:

1. An imaging method, comprising:
   providing an imaging head having a pair of image sensors and a pattern projector;
   providing an illumination source;
   alternating the steps of (a) illuminating an area of interest using an illumination source and (b) projecting a pattern onto the area of interest;
   capturing images of the region of interest during illumination using the illumination source;
   capturing a depth triangulation grid of the region of interest during projection of the pattern;
   identifying first regions in the region of interest that are at a first depth, and identifying second regions in the region of interest that are at a second depth, the first depth different from the second depth, and
   displaying captured image data, wherein the displaying step includes generating a display in which
   the first regions are displayed in a first false color, the first false color being different from a color of said first regions features as captured in the image data, and
   the second regions are displayed in a second false color different from the first false color, the second false color being different from a color of said first regions features as captured in the image data.

2. An imaging method, comprising:
   (a) obtaining an image of a field of interest using a 3D imaging system;
   (b) determining a depth of a structure within the field of interest;
   (c) identifying additional features located at the depth;
   (d) generating an image of the field of interest in which the structure and the additional features are digitally highlighted using a common color, and displaying the generated image.

3. The imaging method of claim 2, wherein the displayed image is a 2D image.

4. The imaging method of claim 2, wherein the structure is a portion of a medical device, and the additional features are tissue.

5. The imaging method of claim 3, wherein structure is an instrument tip moving within the body cavity, and wherein the method further includes repeating steps (a) through (d) such that as the instrument tip is moved within the body cavity, the image updates to visually indicate to the user what tissues lie in the plane of the instrument tip.

6. An imaging method, comprising:
   (a) obtaining an image of a field of interest using at least one camera;
   (b) determining first features at a first depth within the field of interest;
   (c) determining second features at a second depth within the field of interest, the second depth different than the first depth;
   (d) generating an image of the field of interest in which the first features are generated to have a first color that differs from a color of the first features in the image obtained in step (a), and the second features are generated to have a second color that differs from a color of the second features in the image obtained in step (a), wherein the first color and second color are different colors; and
   (e) displaying the generated image.

7. The imaging method of claim 6, wherein said at least one camera comprises a stereoscopic camera pair.

8. The imaging method of claim 7, wherein determining the first and second features includes the step of projecting a pattern onto the field of interest and capturing a depth triangulation grid of the region of interest during projection of the pattern.

* * * * *